(12) United States Patent
Talpalriu et al.

(10) Patent No.: US 6,171,302 B1
(45) Date of Patent: Jan. 9, 2001

(54) APPARATUS AND METHOD INCLUDING A HANDPIECE FOR SYNCHRONIZING THE PULSING OF A LIGHT SOURCE

(76) Inventors: Gerard Talpalriu, 40 Reiness Street, Petach Tikva 49267; Ytzhak Rozenberg, 3 Bergson Street, Tel Aviv 69106; Nissim Hay, 16/262 Bnei Efraim Street, Tel Aviv 69414; Izhak Zobel, 56 Hativat Barel Street, Ra'anana; Martin Abraham, 5 Eshkol Street, Hod Hasharon 45343, all of (IL)

( * ) Notice: Under 35 U.S.C. 154(b), the term of this patent shall be extended for 0 days.

(21) Appl. No.: 09/040,721

(22) Filed: Mar. 18, 1998

Related U.S. Application Data

(60) Provisional application No. 60/041,312, filed on Mar. 19, 1997.

(51) Int. Cl.⁷ ................................................. A61B 18/18
(52) U.S. Cl. .................................. 606/9; 607/89; 33/706
(58) Field of Search ............................. 606/2, 9, 13, 16, 606/17; 607/89, 100; 33/732, 734, 706; 73/1.79, 1.81

(56) References Cited

U.S. PATENT DOCUMENTS

| | | | |
|---|---|---|---|
| 5,200,604 | * | 4/1993 | Rudko et al. ........................ 250/205 |
| 5,325,458 | * | 6/1994 | Morrow et al. . | |
| 5,501,680 | * | 3/1996 | Kurtz et al. .............................. 606/9 |
| 5,611,795 | * | 3/1997 | Slatkine et al. . | |
| 5,628,744 | * | 5/1997 | Coleman et al. ....................... 606/12 |

* cited by examiner

*Primary Examiner*—Linda C. M. Dvorak
*Assistant Examiner*—Roy Gibson
(74) *Attorney, Agent, or Firm*—Eitan, Pearl, Latzer & Cohen-Zedek

(57) ABSTRACT

The present application discloses an apparatus and a method for synchronizing the activation of a light source with the position of a hand piece on a surface and for providing a substantially homogenous exposure of a surface to light irradiation. The apparatus includes a light source, a handpiece for delivering light pulses to the irradiated surface, and a beam delivery system for delivering light from the light source to the handpiece. The handpiece, which is moved along the surface by an operator, includes a sensor for sensing the distance traversed by the handpiece on the surface. The sensor sends signals to a signal processing unit which calculates the distance traversed by the handpiece on the surface and controls the activation of the light source either by automatically activating the light source or by providing the operator with a signal indicating that the light source should be pulsed. The handpiece can also include a device for cooling the irradiated surface and for marking the irradiated part of the surface with a visible marker. The handpiece may be constructed to be movable along a surface in a predetermined orientation relative to the handpiece. Alternatively, the handpiece may be freely movable along the surface in any desired orientation. The light source can be a pulsed laser, a continuous wave laser or a non-coherent light source.

35 Claims, 12 Drawing Sheets

APPARATUS AND METHOD INCLUDING A HANDPIECE FOR SYNCHRONIZING THE PULSING OF A LIGHT SOURCE

This application claims the benefit of U.S. Provisional Application Ser. No. 60/041,312, filed Mar. 19, 1997.

FIELD OF THE INVENTION

The present invention relates to apparatus for enabling controlled activation of a device for treatment of tissue by an operator. The invention is particularly useful for controlling the activation of lasers used for skin treatment, and is therefore described below with respect to this application.

BACKGROUND OF THE INVENTION

A variety of medical and cosmetic treatment methods involve exposure of a defined area of tissue to electromagnetic radiation such as light of various wavelength. The light source can be a non-coherent light source such as a suitable lamp or a coherent light source such as a laser.

The application of lasers for therapeutic or cosmetic skin treatment is known in the art. For example laser radiation is used for facial rejuvenation as disclosed in U.S. Patent Application, titled Laser Facial Rejuvenation, Ser. No. 08/382,918 to Slatkine and Mead filed on Feb. 2, 1995. Another example is the use of laser irradiation for hair removal as disclosed in U.S. Provisional Application Ser. No. 60/008,802 to Slatkine, filed Dec. 18, 1995.

A common feature of many cosmetic and therapeutic tissue treatment methods, including laser irradiation of the skin, is the need to achieve a substantially uniform exposure of the surface of the treated tissue.

Another feature of some of these tissue treatment methods is the need to avoid over-exposure of areas of the treated tissue to the treating radiation. This may be particularly important since the treating light beam is often invisible and does not leave any visible mark on the treated area. For example, when a laser is used for depilating defined skin areas, the operator usually positions a laser light source above the surface of the skin and activates the laser to irradiate a certain predetermined skin area, the operator then advances the laser light source to a new position and activates the laser again to irradiate a new skin area. The operator continues in a similar way until all the area to be treated has been irradiated.

Since the depilating beam does not leave any visible mark on the skin, the operator has to memorize or keep track of the already treated area otherwise he might inadvertently irradiate the same skin area repeatedly, thus causing undesirable over-exposure of the skin. Additionally, it can be difficult to manually control the positioning and activation of the laser light source so as to achieve a uniform irradiation of the skin area without leaving non-irradiated areas or causing undesirable over-exposure of skin areas.

SUMMARY OF THE PRESENT INVENTION

It is therefore an object of the present invention to provide a system for enabling an operator to apply radiation to a surface of tissue in a substantially uniform way and to reduce the risk of over-exposure of the treated tissue by reducing the possibility of repeatedly irradiating the same area of tissue during the same treatment session.

It is another object of the present invention to provide a system for cooling the irradiated tissue for decreasing the heat load of the irradiated tissue and lowering the maximal temperature to which the irradiated tissue is exposed.

It is yet another object of the present invention to provide means for marking the irradiated tissue with a visible mark to inform the operator of the system which areas have been irradiated.

It is still another object of the present invention to provide a stop signal to the operator of the system indicating the desired location of manually irradiating the tissue by the operator.

There is therefore provided in accordance with a preferred embodiment of the present invention a method for synchronizing the activating of a light source with the position of a hand piece on a surface including moving the hand piece along the surface and activating the light source when the hand piece has moved a predetermined distance along the surface.

Yet, in accordance with still another preferred embodiment of the present invention, the method further includes the step of providing a stop signal to the operator when the hand piece has moved the predetermined distance along the surface.

Still, in accordance with another preferred embodiment of the present invention, the step of activating includes activating the light source by an operator when the stop signal is detected by the operator, and the stop signal is an audible signal or a visible signal or a combination thereof.

Further, in accordance with still another preferred embodiment of the present invention, the step of activating also includes the step of scanning the beam of light onto the surface by a scanner.

In accordance with yet another preferred embodiment of the present invention, the method further includes the step of cooling the surface.

There is also provided, in accordance with yet another preferred embodiment of the present invention, a method for providing a substantially homogenous exposure of a surface to light, including moving a hand piece along the surface, activating the light source when the hand piece has moved a predetermined distance along the surface and marking the surface with a visible marker indicating the part of the surface exposed to light.

There is also provided, in accordance with yet another preferred embodiment of the present invention, a system for providing a substantially homogenous exposure of a surface to light including a light delivery handpiece having two ends, a light source connected to a first end of the light delivery handpiece a sensor attached to a second end of the light delivery handpiece for sensing the distance moved by the second end along the surface, and a signal processing unit connected to the sensor and the light source for decoding the output of the sensor and for activating the light source when the second end moves a predetermined distance along the surface.

In accordance with yet another preferred embodiment of the present invention, the signal processing unit also provides a stop signal to an operator when the second end has moved a predetermined distance along the surface.

Further, in accordance with still another preferred embodiment of the present invention, the signal processing unit activates the light source when the second end has moved a predetermined distance along the surface, only when manually activated by the operator.

Still further, in accordance with yet another preferred embodiment of the present invention, the system includes a marking device for marking the surface with a visible marker indicating the part of the surface which has been exposed to light.

yet further, in accordance with still another preferred embodiment of the present invention, the system includes a device for cooling the surface.

Still further, in accordance with yet another preferred embodiment of the present invention, the system includes a beam delivery system connecting the first end of the light delivery handpiece to the light source.

additionally, in accordance with yet another preferred embodiment of the present invention, the beam delivery system is an articulated arm or an optical fiber or an optical fiber bundle or a hollow waveguide.

In accordance with another preferred embodiment of the present invention, the predetermined distance is determined by the size and energy distribution profile of the spot of light produced by the light source on the surface to provide a substantially uniform exposure of part of the surface to light from the light source.

In accordance with yet another preferred embodiment of the present invention, the surface is the surface of a tissue.

In accordance with still another preferred embodiment of the present invention, the light source is a pulsed laser. In accordance with still another preferred embodiment of the present invention, the light source is a continuous wave laser.

In accordance with yet another preferred embodiment of the present invention, the light source is an incoherent light source.

There is therefore also provided, in accordance with yet another preferred embodiment of the present invention, a handpiece including a hollow member having a first end and a second end, and a sensor attached to the first end of the hollow member for sensing the movement of the handpiece along a surface and for providing signals representing the sensed movement, the second end of the hollow member being connectable to a light source.

In accordance with another preferred embodiment of the present invention the hollow member also includes at least one optical element for directing light from the light source to the surface.

In accordance with yet another preferred embodiment of the present invention, the optical element is an optical fiber or an optical fiber bundle or a hollow waveguide or a lens or any combination thereof.

In accordance with still another preferred embodiment of the present invention, the handpiece includes a rotatable member rotating by moving the handpiece along the surface.

In accordance with yet another preferred embodiment of the present invention, the rotatable member is rotatably attached to the first end of the hollow member and is made of a material which is substantially transparent to light emitted from the light source. The rotatable member is positioned at the first end of the hollow member such that the light emitted from the light source passes through the rotatable member prior to striking the surface.

In accordance with another preferred embodiment of the present invention, the transparent rotatable member is hollow, enabling a cooling fluid to be circulated therewithin for cooling the surface while the rotatable member is in contact therewith.

In accordance with still another preferred embodiment of the present invention, the handpiece also includes a marking device for marking the surface while the handpiece is being moved therealong.

In accordance with still another preferred embodiment of the present invention, the second end of the hollow member is connectable to the light source through a scanner.

Yet, in accordance with another preferred embodiment of the present invention, the handpiece is sterilizable.

Still, in accordance with yet another preferred embodiment of the present invention, the rotatable member is disposable.

Furthermore, in accordance with still another preferred embodiment of the present invention, the rotatable member is sterilizable.

Furthermore, in accordance with still another preferred embodiment of the present invention, the hollow member of the handpiece further includes a visible mark for indicating the orientation required for moving the handpiece along the surface.

Further yet, in accordance with still another preferred embodiment of the present invention, the hollow member of the handpiece is shaped to have a distinctly visible polarity for indicating the orientation required for moving the handpiece along the surface.

Finally, in accordance with still another preferred embodiment of the present invention, the handpiece can be oriented in any selected orientation relative to the direction of its movement along the surface while the longitudinal axis of the handpiece is being held substantially perpendicular to the surface.

BRIEF DESCRIPTION OF THE DRAWINGS

The present invention will be understood and appreciated more fully from the following detailed description taken in conjunction with the drawings in which.

DETAILED DESCRIPTION OF A PREFERRED EMBODIMENT

It will be appreciated that, while the system disclosed hereinbelow is described as using a pulsed or a continuous wave laser as the source of electromagnetic radiation, the system can be used with any other suitable radiation sources such as any source of continuous or pulsed light or other sources of non-coherent electromagnetic radiation or any other source of radiation useful for therapeutic or cosmetic purposes. Thus, the term light refers throughout the specification and claims not only to visible light but to any of the radiation types referred to hereinabove.

Figure 1:
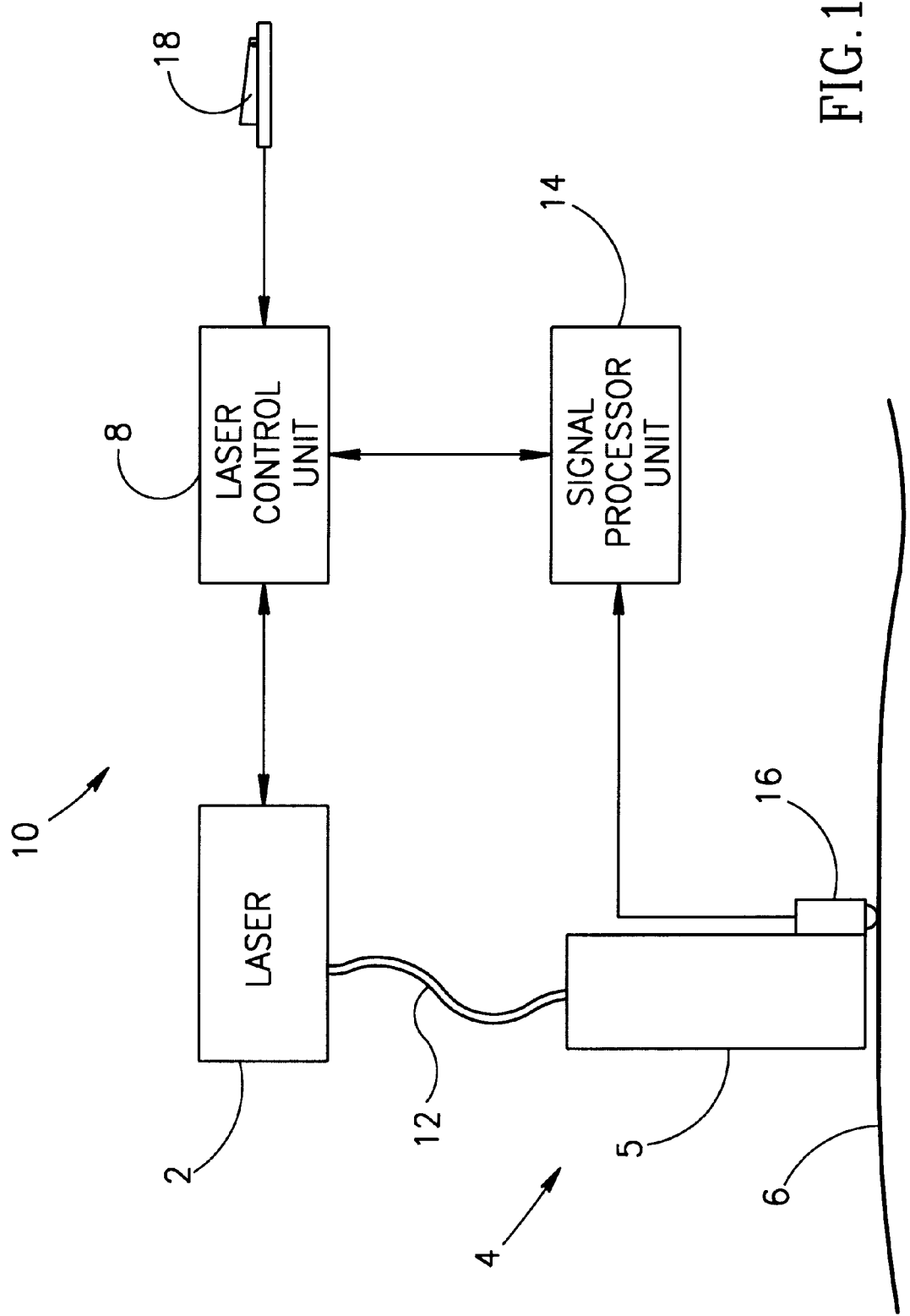
FIG. 1 is a schematic block diagram illustrating a system for controlling the exposure of a surface of a tissue to laser radiation in accordance with a preferred embodiment of the present invention.

Reference is now made to FIG. 1 which is a schematic block diagram illustrating a system 10 for controlling the exposure of a surface of a tissue to laser radiation in accordance with a preferred embodiment of the present invention. System 10 includes a laser 2 connected to a handpiece 4 by a suitable beam delivery system 12. The beam delivery system 12 can be any suitable delivery system such as an optical fiber, an optical fiber bundle or a suitable waveguide such as the hollow waveguide disclosed in U.S. Pat. No. 5,325,458 to Morrow et al. The handpiece 4 includes a hollow member 5 enabling the laser light to pass within it and strike the surface 6 of the tissue that is to be irradiated.

It is noted that while the laser 2 of FIG. 1 is connected to the handpiece 4 through the beam delivery system 12, other preferred embodiments are possible in which the laser 2 is coupled directly (not shown) to the handpiece 4. The handpiece 4 can also include optical elements (not shown) for suitably directing the laser light beam onto the surface 6. These optical elements are constructed to direct a laser light spot at the surface 6, the spot having a desired size and shape suitable for the specific therapeutic or cosmetic application.

The handpiece 4 also includes a sensor assembly 16 attached to the hollow member 5 for sensing the translation of the handpiece along the surface 6. The sensor assembly can include any type of sensor suitable for generating signals which can be used to determine the distance traversed by the handpiece 4 on the surface 6, such as a mechanical or an optical encoder as disclosed in detail hereinafter. The system 10 also includes a signal processor 14 suitably connected to the sensor assembly 16 and laser control unit 8 connected to the signal processor 14 and to the laser 2. The system 10 also includes an actuating switch 18 which can be any suitable switch such as a foot pedal. When the actuating switch 18 is depressed by the operator, the laser 2 can be activated by the laser control unit 8. Thus, activating the laser is enabled as long as the actuating switch is held depressed by the operator. The actuating switch thus serves as a safety measure against accidental activation of the laser.

When the handpiece 4 is moved across the surface 6 of the tissue the sensor assembly 16 senses the translational movements of the handpiece 4 and sends suitable signals to the signal processor 14. The signal processor 14 processes the signals of the sensor assembly 16 and calculates the distance traversed by the handpiece from the last position at which the laser was activated.

Initially, the operator puts the handpiece 4 on the surface 6 and depresses the actuating switch 18 to activate the laser and irradiate the area underneath the handpiece. At this stage the operator can be assisted by a low power indicating light beam (not shown) to view the area which will be irradiated before activating the laser. The operator can observe the indicating light through suitable openings (not shown) in the hollow member 5. The operator then moves the handpiece on the surface 6. The sensor assembly 16 sends signals to the signal processor which calculates the distance traversed by the handpiece on the surface 6. The signal processor also calculates the required distance to the next desirable area for irradiation by taking into account the dimensions of the irradiated spot and the degree of the overlap of two adjacent irradiated spots required to achieve a substantially uniform exposure to the radiation. This overlap can be necessary when the irradiating energy is non-uniformly distributed within the irradiated spot. For example, The energy density can have a gaussian distribution profile along the diameter of a circular irradiated spot.

When the distance traversed by the handpiece equals the calculated optimal irradiation distance, the signal processor alerts the operator by issuing a stop signal. The stop signal can be a suitable sound such as a beep tone or a visual signal such as the lighting up of an indicator light or a combination of a sound and a visual signal. The stop signal indicates to the operator that the handpiece has reached the next area to be irradiated. If the laser is ready for activation, the system automatically activates the laser. Once the laser is activated, the stop signal is turned off and the user can continue to move the handpiece 4, repeating the sequence of steps described hereinabove, thus exposing consecutive areas of the tissue surface.

This method is suitable for pulsed lasers having a low pulsing frequency, such as a ruby laser. The stop signal instructs the operator to stop moving the handpiece until the laser is ready for delivering another pulse. It is noted that, if a laser having a higher pulse frequency is used with the system 10, the stop signal is rendered unnecessary since the laser will be capable of automatically delivering a pulse each time the handpiece traverses a distance equal to the calculated optimal distance between two irradiated spots. Thus, when using a laser with a higher pulsing frequency, the operator can move the handpiece 4 while the laser is being automatically activated by the signal processor to irradiate a portion of the surface 6 such as a substantially linear stripe or any other suitable portion of the surface 6.

After the completion of irradiating of one such portion the operator can reposition the handpiece 4 at a new position on the surface 6 and proceed to similarly irradiate another portion of the surface 6, such as a new substantially linear stripe parallel to the previously irradiated first line. Thus, the operator can achieve a substantially complete irradiation of the tissue surface 6, while avoiding serious overexposure of surface areas, by repeating the above procedure until the desired area of the surface 6 is satisfactorily treated.

It is noted that, while the method disclosed hereinabove uses a pulsed laser, the method can also be used with a continuous wave laser. The continuous wave laser can be activated for relatively brief periods of continuous operation. It is further noted that, the periods of continuous operation of the continuous wave laser can be substantially longer than the typical pulse duration of pulsed lasers such as ruby lasers.

It is noted that, for a better understanding, like components are designated by like reference numerals throughout the various figures.

Figure 2:
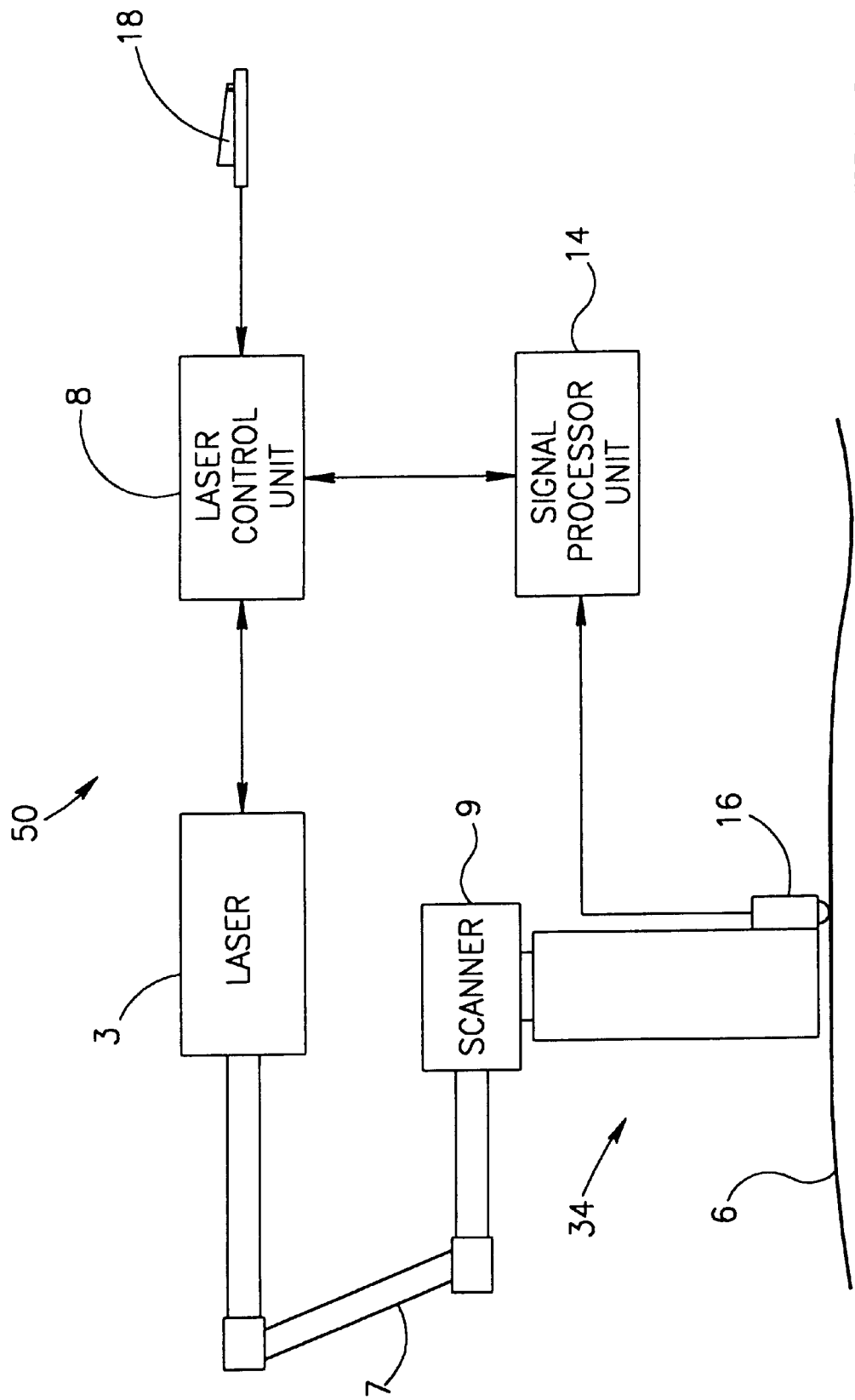
FIG. 2 is a schematic block diagram illustrating a system for controlling the exposure of a surface of a tissue to laser radiation in accordance with another preferred embodiment of the present invention.

Reference is now made to FIG. 2 which is a schematic block diagram illustrating a system 50 for controlling the exposure of a surface of a tissue to laser radiation in accordance with another preferred embodiment of the present invention.

System 50 is similar to system 10 of FIG. 1 except that laser 2, beam delivery system 12 and handpiece 4 of FIG. 1 are replaced by a laser 3, an articulated arm delivery system 7, a scanner 9 and a handpiece 34. Handpiece 34 operates similarly to handpiece 4 of FIG. 1 to control the exposure of the surface 6 to laser radiation as disclosed hereinabove, except that it is attached to the scanner 9. Thus, while in FIG. 1 the laser creates a spot of laser light on surface 6, the system 50 of FIG. 2 scans a laser beam along a defined area of surface 6 which underlies handpiece 34.

Figure 3:
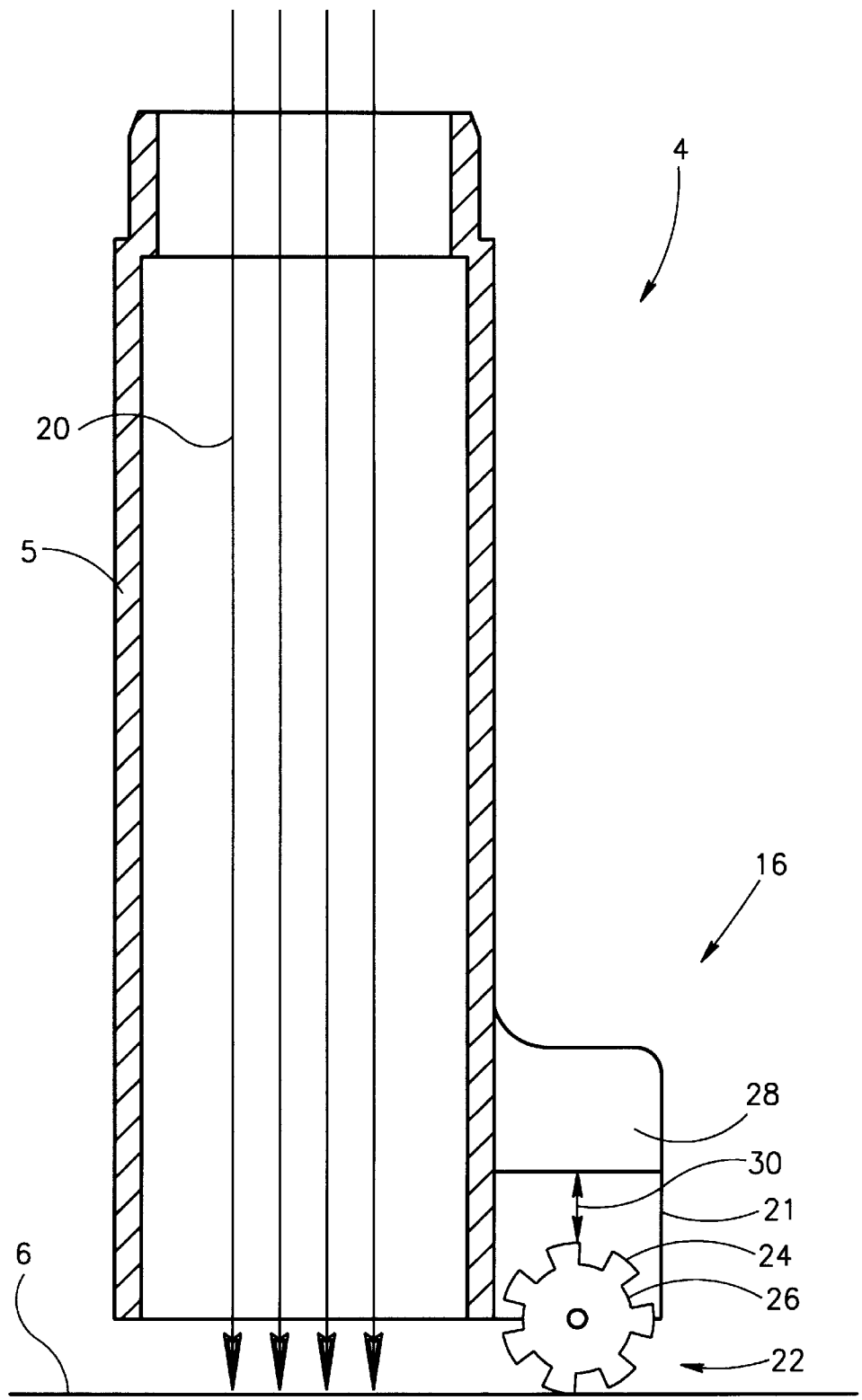
FIG. 3 is a schematic longitudinal cross section illustrating the handpiece of FIG. 1 in detail, in accordance with a preferred embodiment of the present invention.

Reference is now made to FIG. 3 which is a schematic longitudinal cross section of the handpiece 4 of FIG. 1, illustrating the sensor assembly 16 in detail in accordance with a preferred embodiment of the present invention. The hollow member 5 is a cylindrical hollow tube through which a laser light beam 20 can pass to strike the part of the surface 6 lying underneath the handpiece 4. The sensor assembly 16 is attached to one end of the hollow member 5. The sensor assembly 16 includes a housing 21 and a cogwheel shaped rotatable member 22 rotatably attached to housing 21. Rotatable member 22 can be placed in contact with the surface 6 and rolled therealong. The rotatable member 22 has equally spaced notches 26 therein separated by areas 24. The sensor assembly 16 also includes an optical sensor 28 detachably attached to the housing 21. The optical sensor can be any suitable optical sensor such as the reflective object sensor model OPB 706A commercially available from Optek Technology, Inc. TX, U.S.A., that includes an infra-red light source and a light detector (not shown). The optical sensor 28 can be detached from the housing 21 so that the handpiece 4 can be sterilized.

The optical sensor 28 radiates an infrared light beam 30 that hits the surface of the rotatable member 22 underlying it and is reflected therefrom to reach the light detector of the optical sensor 28. If the light beam is reflected from one of the areas 24, the intensity of the reflected light is sufficient to activate the optical sensor 28 to send an "on" signal to the signal processor unit 8. If the light beam is reflected from the surface at the bottom of one of the notches 26, the intensity of the light reflected from that bottom surface is not sufficient to activate the optical sensor 28, and the optical sensor 28 sends an "off" signal to the signal processor unit 8. The signal processing unit 8 uses the on and off signals, which are represented by different predetermined voltage values, to calculate the distance traversed by the handpiece 4 on the surface 6 and to determine the next location for firing the laser 2 as disclosed in detail hereinabove.

It is noted that although the rotatable member 22 of the preferred embodiment of FIG. 3 is cogwheel shaped, other rotatable members can be used such as a rotatable member having a circular or polygonal cross section or any other rotatable member that can be rolled along the surface 6 without substantial slip and that has on its surface alternating areas having suitably different reflectivity values that can be differentiated by the optical sensor 28. A non limiting example is a rotatable member having alternating rough and smooth areas which have substantially different reflectivity values at the wavelength of light used by the optical sensor 28. Another non limiting example is a rotatable member made of a highly reflective metal and having equally spaced stripes of a plastic having low reflectivity embedded therein.

It is noted that, the rotatable member 22 can be made from a sterilizable material such as a metal. In a non limiting example rotatable member 22 is made from aluminum. Rotatable member 22 is detachably attached to the housing 21 and can be detached therefrom. This facilitates the sterilization of rotatable member 22. Alternatively, rotatable member 22 can be disposable and can be replaced before using the handpiece 4 for treating a new patient.

Figure 4:
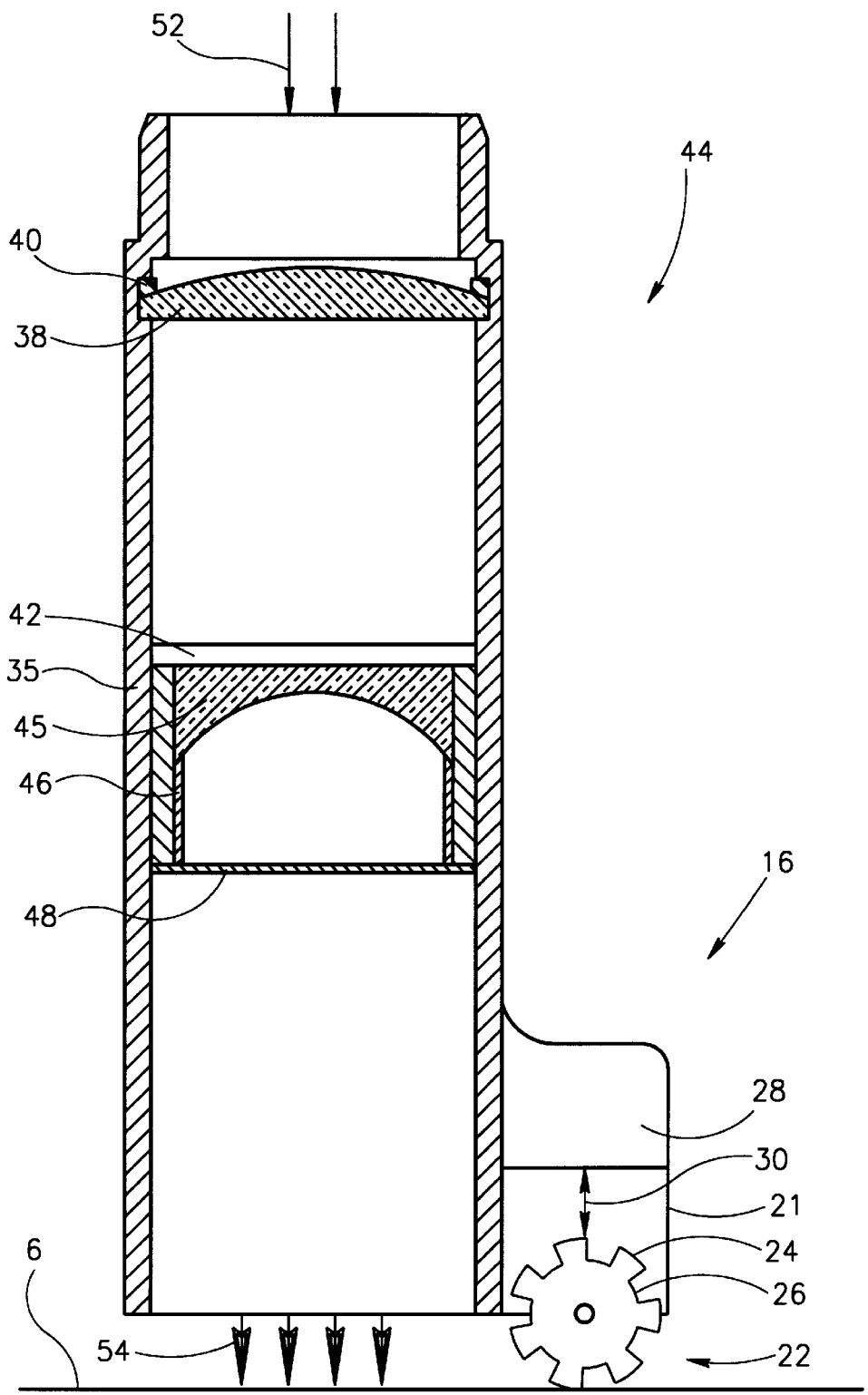
FIG. 4 is a schematic cross section illustrating a handpiece constructed and operative in accordance with another preferred embodiment of the present invention.

Reference is now made to FIG. 4 which is a schematic cross section illustrating a handpiece 44, constructed and operative in accordance with another preferred embodiment of the present invention. Handpiece 44 can be used instead of handpiece 4 in system 10 of FIG. 1. Handpiece 44 includes a hollow member 35 and a sensor assembly 16 attached thereto. The sensor assembly 16 is constructed and operative in determining the distance traversed by handpiece 44 along surface 6 as disclosed hereinabove. Handpiece 44 further includes an upper lens 38 secured within the hollow member 35 by a lens holder 40. Handpiece 44 also includes a lower lens 45 secured within the hollow member 35 by a lens holder 42. Handpiece 44 further includes a protective window 48 and a spacer 46 disposed between the lower lens 45 and the protective window 48. Lenses 38 and 45 modify the incoming laser beam 52 so that the outgoing laser beam 54 has the appropriate energy density required for treatment of surface 6.

Figure 5:
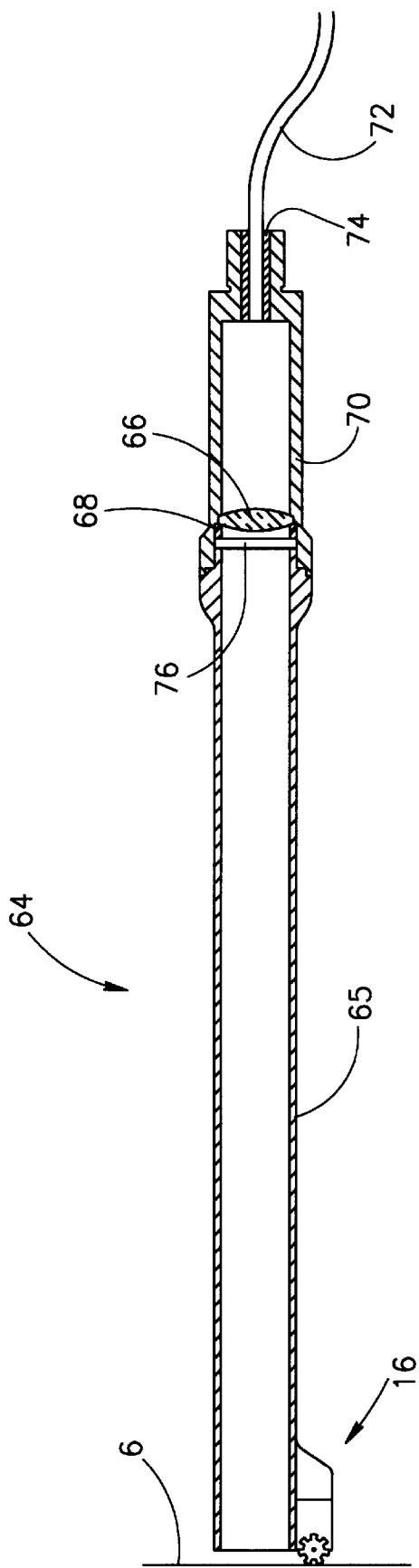
FIG. 5 is a schematic cross section illustrating a handpiece using a laser beam delivered by an optical fiber, constructed and operative in accordance with yet another preferred embodiment of the present invention.

Reference is now made to FIG. 5 which is a schematic cross section illustrating a handpiece 64, using a laser beam delivered by an optical fiber, constructed and operative in accordance with yet another preferred embodiment of the present invention. Handpiece 64 can be used instead of handpiece 4 in system 10 of FIG. 1. Handpiece 64 includes an applicator 65 and a sensor assembly 16 attached thereto. The sensor assembly 16 is constructed and operative in determining the distance traversed by handpiece 64 along surface 6 as disclosed hereinabove. Handpiece 64 also includes a fiber adapter 70 attached to applicator 65. Fiber adapter 70 further includes an optical fiber 72 for guiding a laser beam from laser source 2 of FIG. 1 into the handpiece 64. Optical fiber 72 is connected to the fiber adapter 70 by fiber connector 74. Fiber adapter 70 further includes a lens 66 secured within the fiber adapter 70 by a lens holder 68. Fiber adapter also includes a protective window 76 for protecting the lens 66. Lens 66 modifies the laser beam exiting from optical fiber 72 so that it has the appropriate energy density required for treatment of surface 6.

Figure 6:
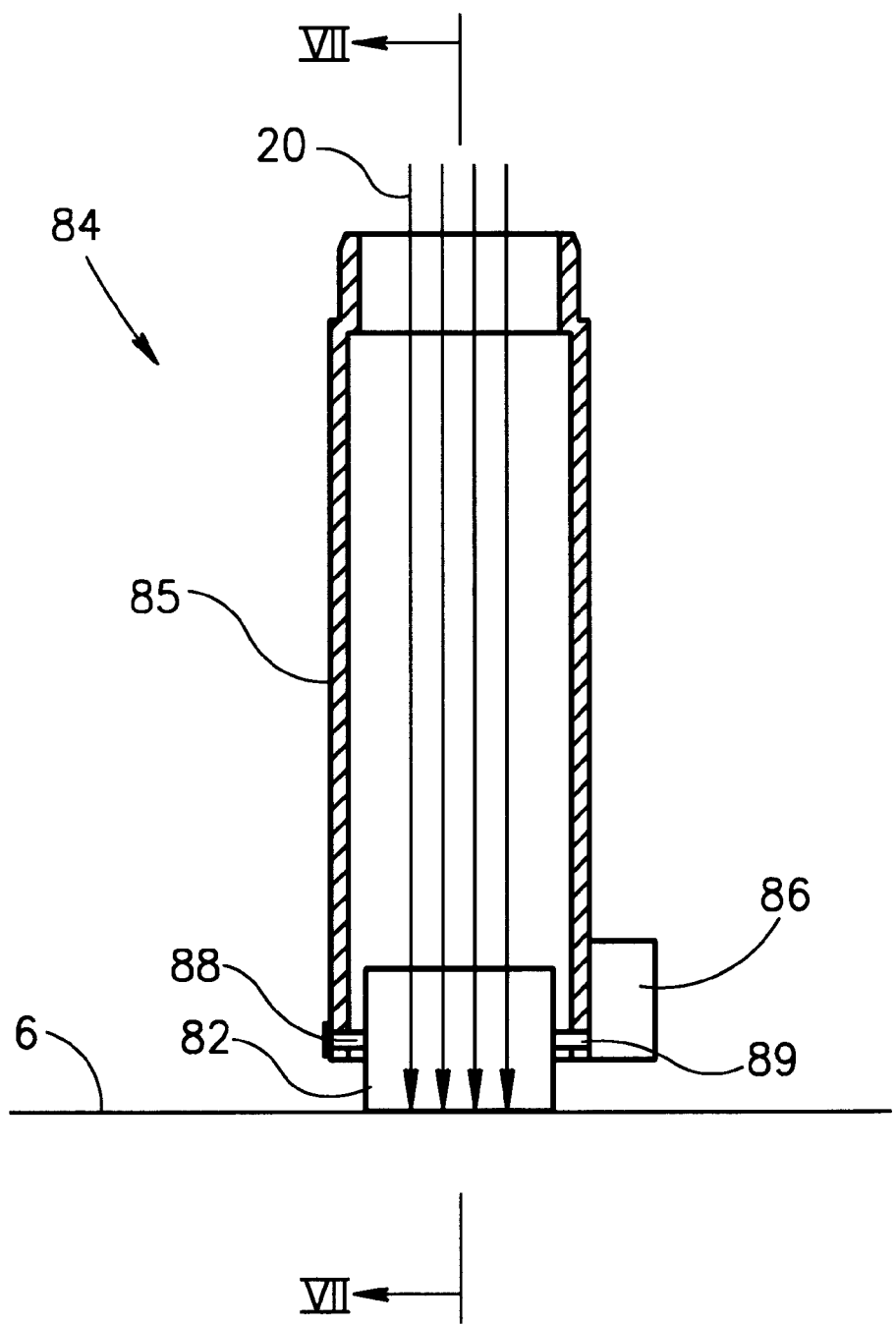
FIG. 6 is a schematic cross section illustrating a handpiece having a transparent rotatable member in accordance with another preferred embodiment of the present invention.

Reference is now made to FIG. 6 which is a schematic cross section illustrating a handpiece 84 constructed and operative to control the exposure of a surface of a tissue to laser radiation in accordance with still another preferred embodiment of the present invention.

Handpiece 84 includes a hollow member 85 and a rotatable member 82 rotatably attached to hollow member 85 by two axles 88 and 89. Axle 89 is also connected to a sensor 86 for sensing the distance traversed by the rotatable member 82 along surface 6. The sensor 86 can be any suitable sensor such an electro-optical sensor or a hall effect sensor for sensing the rotation of axle 89 and encoding the rotation into appropriate signals. The signals from sensor 86 are sent to a suitable signal processor unit such as the signal processor unit 8 of FIG. 1 for calculating the distance traversed by the handpiece 84, taking into account the diameter of the rotatable member 82, as disclosed hereinabove. The rotatable member 82 is made of a material that is substantially transparent to the wavelength of light beam 20 such as suitable transparent plastic or suitable glass. The laser light 20 thus passes through rotatable member 82 to strike an area of surface 6 underlying rotatable member 82.

Figure 7:
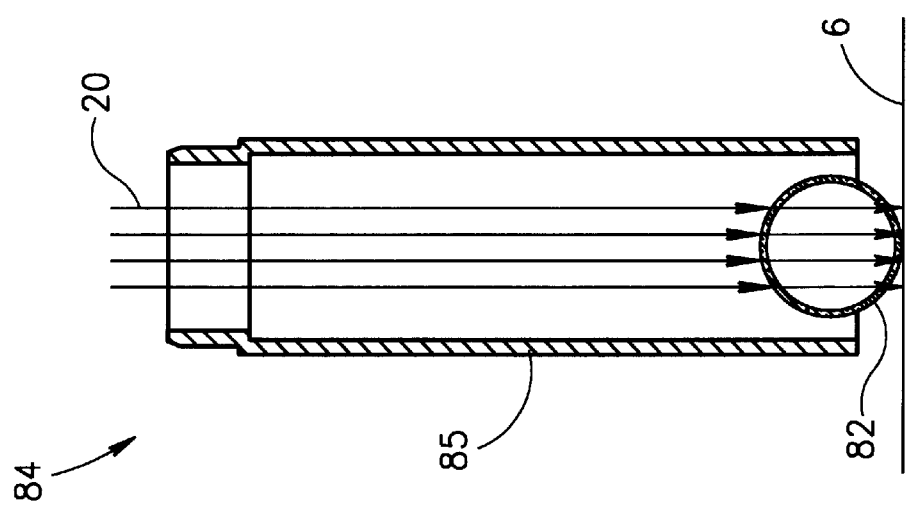
FIG. 7 is a cross section of the handpiece of FIG. 6 taken along the lines VII—VII.

Rotatable member 82 is cylinder shaped, as can be seen in FIG. 7, to which reference is now briefly made. FIG. 7 is a cross section of handpiece 84 of FIG. 6, taken along the lines VII—VII.

Figure 8:
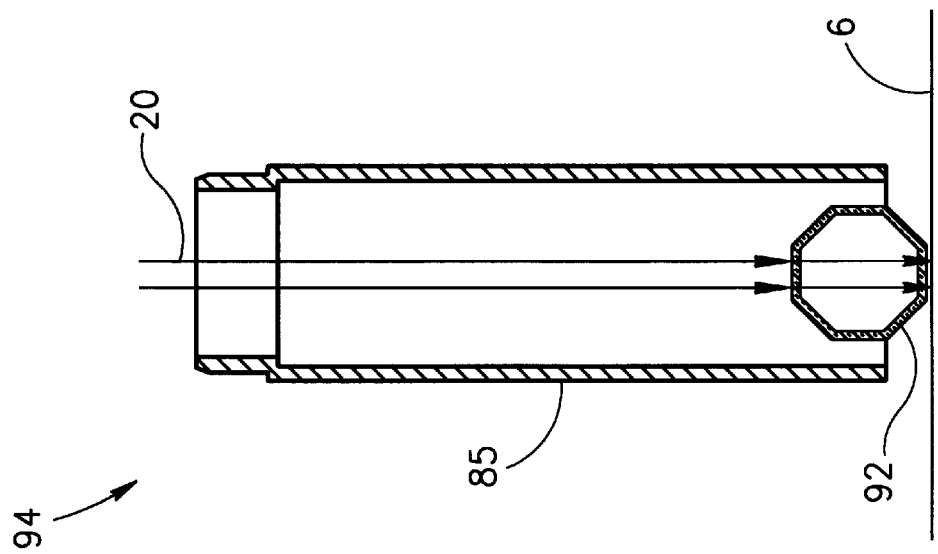
FIG. 8 is a schematic cross section illustrating a handpiece having a rotatable member with an octagonal cross section in accordance with another preferred embodiment of the present invention.

Reference is now made to FIG. 8 illustrating a schematic cross section of a handpiece 94 in accordance with another preferred embodiment of the present invention. Handpiece 94 is similar to handpiece 84 of FIGS. 6 and 7, except that it includes a transparent rotatable member 92 having an octagonal cross section in contrast to the rotatable member 82 of handpiece 84 which has a circular cross section (FIG. 7). This preferred embodiment has an advantage of diminishing the distortion of the laser beam 20 as it passes through the transparent rotatable member.

It is noted that the transparent rotatable member 82 of handpiece 84 can have any other suitable cross section and can be made of any suitable material which is substantially transparent to the light beam 20.

Figure 9:
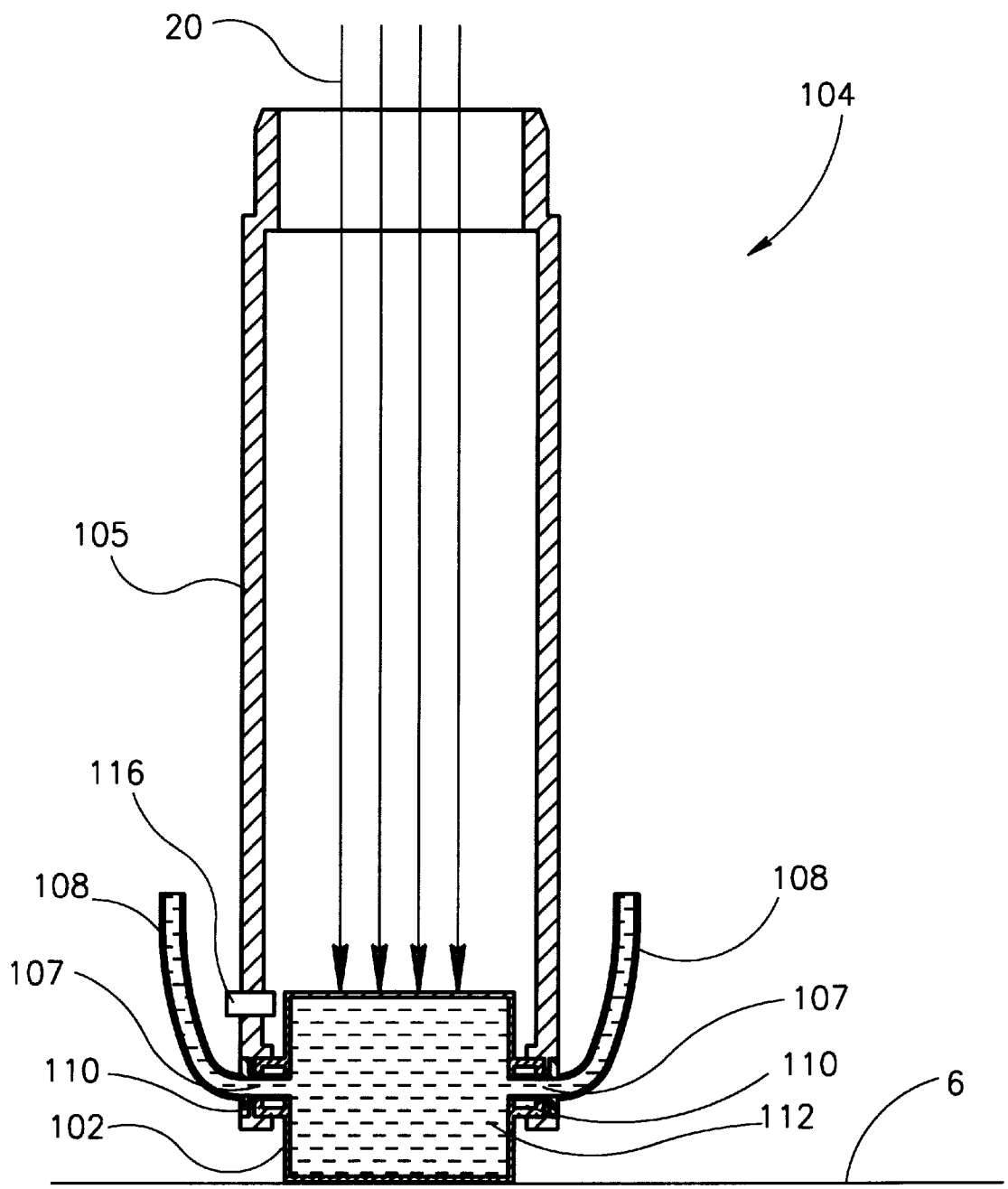
FIG. 9 is a schematic cross section illustrating a handpiece constructed and operative to control the exposure of a surface of a tissue to laser radiation and to cool the tissue in accordance with still another preferred embodiment of the present invention.

Reference is now made to FIG. 9 which is a schematic cross section illustrating a handpiece 104 constructed and operative to control the exposure of a surface of a tissue to laser radiation and to cool the tissue in accordance with still another preferred embodiment of the present invention. Handpiece 104 includes a hollow member 105 having a rotatable member 102 rotatably attached thereto. Rotatable member 102 is hollow and can rotate within the hollow member 105 on two hollow axles 107. Each of the hollow axles 107 is connected to a flexible tube 108 by a leak-proof rotating connector 110. During operation, the hollow rotatable member 102 is filled with a cooling fluid 112 which is pumped through the hollow rotatable member 102 by a suitable pump (not shown) through one of the flexible tubes 108 and leaves the hollow rotatable member 102 through the other flexible tube 108. Thus, when the handpiece 104 is moved along surface 6 the hollow rotatable member 102 rolls along surface 6 and cools the tissue underlying it. The hollow rotatable member 102 and the cooling fluid 112 are substantially transparent to the laser beam 20 which passes through them to strike the underlying surface 6. An advantage of this preferred embodiment of the present invention is that the cooling of the tissue decreases the heat load of the irradiated tissue and lowers the maximal temperature to which the irradiated tissue is exposed, thus avoiding burns to the upper layers of the tissue during the irradiation treatment.

The Handpiece 104 also includes a sensor 116 which senses the movement of the hollow rotatable member 102 as it rolls along surface 6. Sensor 116 can be any suitable type of sensor. A non-limiting example is the optical sensor such as the reflective object sensor model OPB 706A disclosed hereinabove (FIG. 3). Sensor 116 can operate by sensing the reflectivity of areas on the surface of hollow rotatable member 102 having alternating high and low reflectivity values (The alternating areas are not shown in FIG. 9 for the sake of clarity of illustration). These alternating areas face the detector (not shown) of sensor 116.

It is noted that the hollow rotatable member 102 of handpiece 104 can have any suitable cross section such as a circular or a polygonal cross section.

It is further noted that the cooling fluid 112 can be any suitable cooling fluid such as water, a suitable salt solution, an solution of glycerol in water or any other cooling fluid which is substantially transparent to the laser beam 20.

Figure 11:
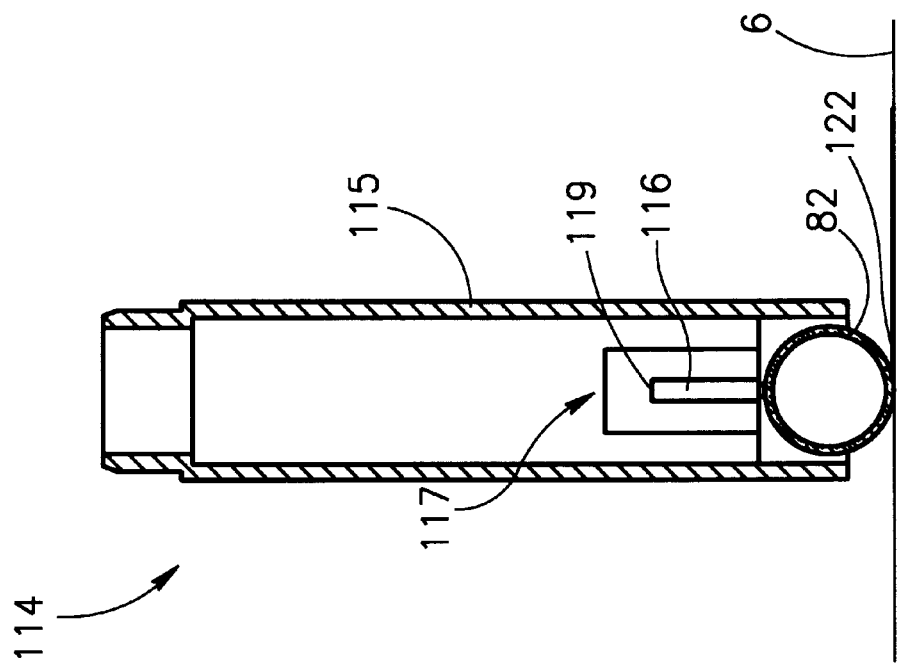
FIG. 11 is a schematic cross section of a different view of the handpiece of FIG. 10
Figure 10:
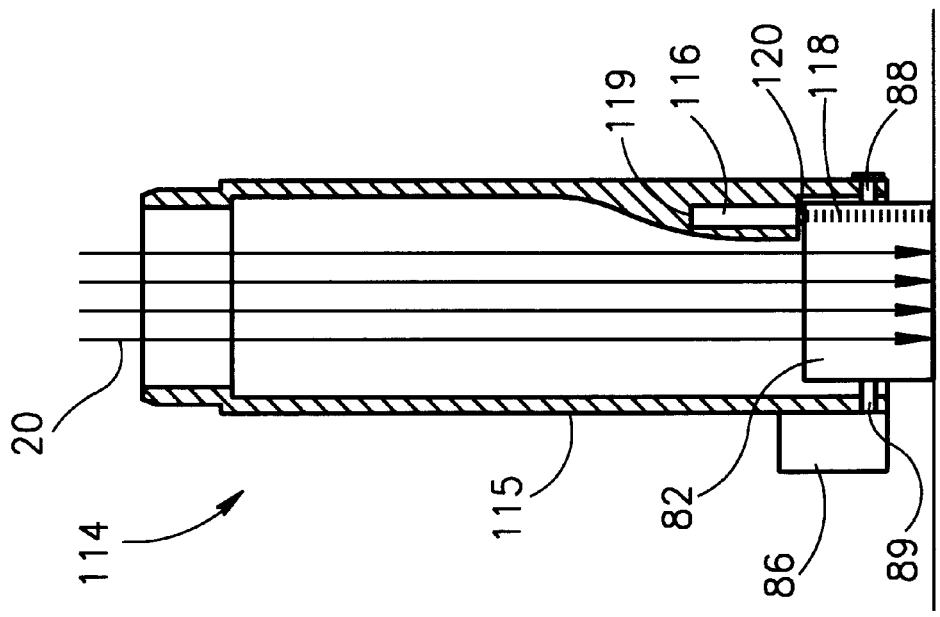
FIG. 10 is a schematic cross sections illustrating a handpiece for controlling the exposure of a surface of a tissue to laser radiation and for marking the surface with a marker in accordance with another preferred embodiment of the present invention.

Reference is now made to FIGS. 10 and 11 which are schematic cross sections illustrating a handpiece 114 constructed and operative to control the exposure of a surface of a tissue to laser radiation and to mark the surface with a marker in accordance with another preferred embodiment of the present invention.

Turning to FIG. 10, Handpiece 114 includes a hollow member 115 having a rotatable member 82 rotatably attached thereto. Rotatable member 82 is connected to a sensor 86 and operates in sensing the distance traversed by the handpiece 114 as disclosed in detail for handpiece 84 of FIG. 6 hereinabove.

Hollow member 115 also includes a marking device 117 (FIG. 11) for marking the surface 6 with a visible marker. Marking device 117 includes a replaceable container 119 containing a marker 116 therewithin. Marker 116 can be any marking fluid suitable for leaving a visible trace upon surface 6 of the tissue. Marking device 117 further includes a marking tip 120 which is in contact with rotatable member 82. When handpiece 114 is moved along surface 6, marking tip 120 transfers some of marker 116 onto the surface of rotatable member 82, thus, depositing a marker film 118 on rotatable member 82. As the rotatable member is rolled along surface 6, part of the marker 116 of marker film 118 is transferred to surface 6, creating a visible marker trace 122 therealong. Visible marker trace 122 has the advantage of providing the operator of handpiece 114 with a visible mark assisting the operator in observing the areas of the surface 6 which have been irradiated, thus helping in preventing accidental over-exposure of areas which have been already irradiated. A further advantage of visible marker trace 122 is that it assists the operator of handpiece 114 in obtaining a relatively uniform exposure of the area to be treated by providing a visible track parallel to which the operator can align the movement of handpiece 114 for irradiating the next part of surface 6.

It is noted that the marking device 117 can be any suitable marking device such as a replaceable cartridge a refillable cartridge or any other marking device capable of suitably transferring marker 116 to surface 6.

Figure 12:
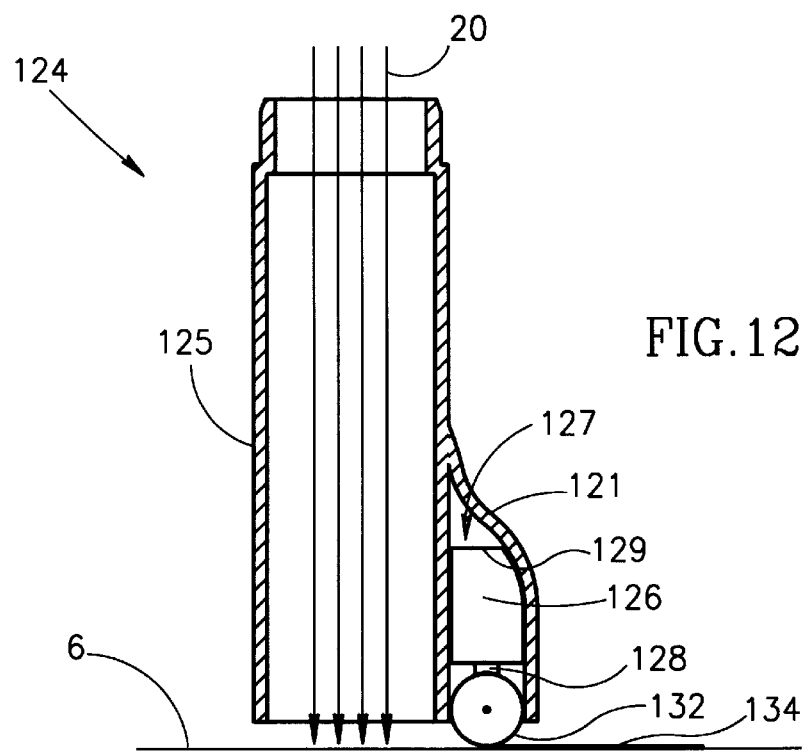
FIG. 12 is a schematic cross section illustrating a handpiece constructed and operative to control the exposure of a surface of a tissue to laser radiation and to mark the surface with a marker in accordance with still another preferred embodiment of the present invention.
Figure 13:
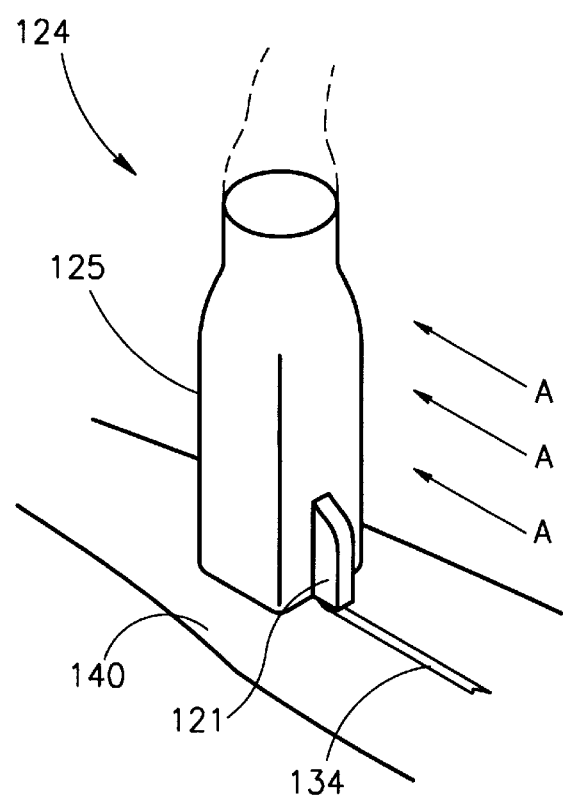
FIG. 13 is a schematic isometric view of the handpiece of FIG. 12.

Reference is now made to FIGS. 12 and 13. FIG. 12 is a schematic cross section illustrating a handpiece 124 constructed and operative to control the exposure of a surface of a tissue to laser radiation and to mark the surface with a marker in accordance with still another preferred embodiment of the present invention and FIG. 13 is a schematic isometric view of the handpiece 124 of FIG. 12.

Turning to FIG. 12, Handpiece 124 includes a hollow member 125 having a housing 121 attached thereto. Housing 121 includes a rotatable member 132 rotatably attached thereto. Rotatable member 132 is connected to a sensor (not shown for the sake of clarity of illustration) and operates in sensing the distance traversed by the handpiece 114 as disclosed in detail for handpiece 84 of FIG. 6 hereinabove.

Housing 121 also includes a marking device 127 for marking the surface 6 with a visible marker. Marking device 127 includes a replaceable container 129 containing a marker 126 therewithin. Marking device 127 further includes a marking tip 128 which is in contact with rotatable member 132. When handpiece 124 is moved along surface 6, marking tip 128 transfers some of marker 126 onto the surface of rotatable member 132, thus, depositing a marker film (not shown) thereon. As the rotatable member 132 is rolled along surface 6, part of the marker 126 of the marker film is transferred from rotatable member 132 to surface 6, creating a visible marker trace 134 therealong.

FIG. 13 illustrates the handpiece 124 of FIG. 12 being moved along the skin surface 140 of a hand. The handpiece 124 is moved along the skin surface 140 in the direction of the arrows labeled A. also shown is the visible marker trace 134 which is left on the skin surface 140 by the handpiece 124.

It is noted that in contrast to handpiece 114 of FIG. 10, in which the laser beam 20 passes through the transparent rotatable member 82 before striking the surface 6, in handpiece 124 laser beam 20 passes through the hollow member 125 and strikes the surface 6 without passing through the rotatable member 132.

It is noted that the handpieces 4, 44, 64, 84, 94, 104, 114, and 124 of FIGS. 3, 4, 5, 6, 8, 9, 10 and 12, respectively, are designed to be oriented in a specific direction while being moved along the surface 6. This orientation is determined by the preferred direction of rotation of the rotatable member of the handpiece. For example, the handpiece 4 of FIG. 3 has to be oriented such that the axis around which the rotatable member 22 rotates is perpendicular to the direction along which the handpiece 4 is moved. Similarly, the handpiece 114 of FIG. 10 has to be oriented such that the axis around which the rotatable member 82 rotates is perpendicular to the direction along which the handpiece 114 is moved.

Various methods can be used to enable the operator of the system to properly orient the handpiece while it is being moved along the surface. According to one embodiment of the present invention example, visibly discernible "landmarks" existing on the handpiece can be used for proper orientation. This is best seen in FIG. 13 where the housing 121 protrudes from the handpiece 124, thus, indicating the required orientation of movement labeled by arrows A. In handpieces having no visibly discernible landmarks, such landmarks can be added. In accordance with one embodiment of the present invention, a stripe of color can be painted on the outer surface of the handpiece (not shown) to indicate the required orientation. In accordance with one embodiment of the present invention, the handpiece can be shaped such that it has a distinctly discernible polarity indicating the required orientation. For example, at least part of the hollow member 85 of handpiece 84 (FIG. 7) can have a "teardrop" like cross-section (not shown) with the pointed part thereof indicating the required orientation for moving the handpiece 84 along the surface 6.

While the methods disclosed hereinabove facilitate the identification of the required orientation of the handpieces during movement, in some cases it may be desirable to use a handpiece that can be moved in any selected direction along the surface 6 without having to be oriented in a particular direction prior to being moved along the surface 6.

Figure 14:
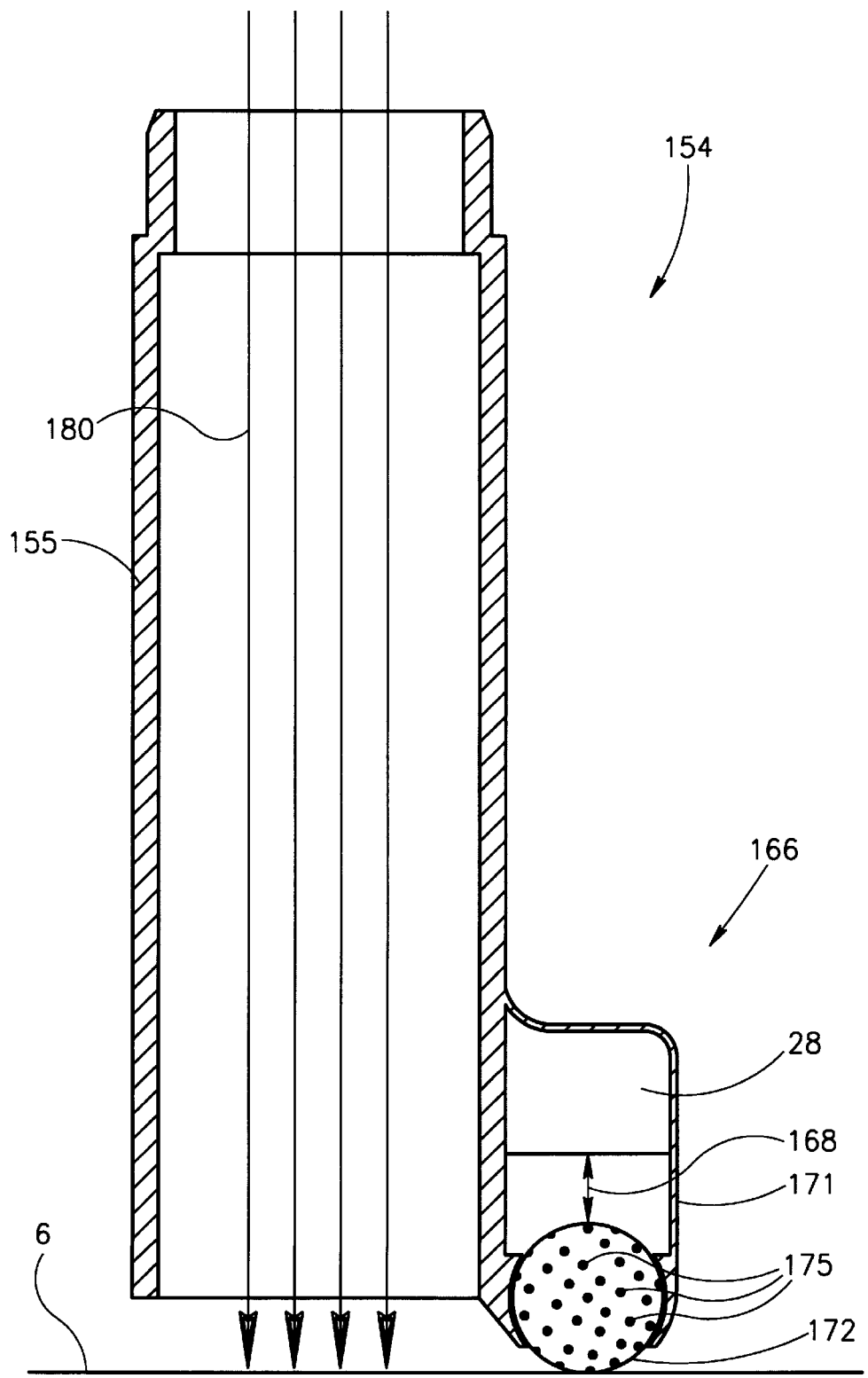
FIG. 14 is a schematic cross section illustrating a handpiece having a multi-directional sensor enabling controlling the exposure of a surface of a tissue to laser radiation while the handpiece is being moved in any orientation along the surface of the tissue, in accordance with another preferred embodiment of the present invention.
Figure 15:
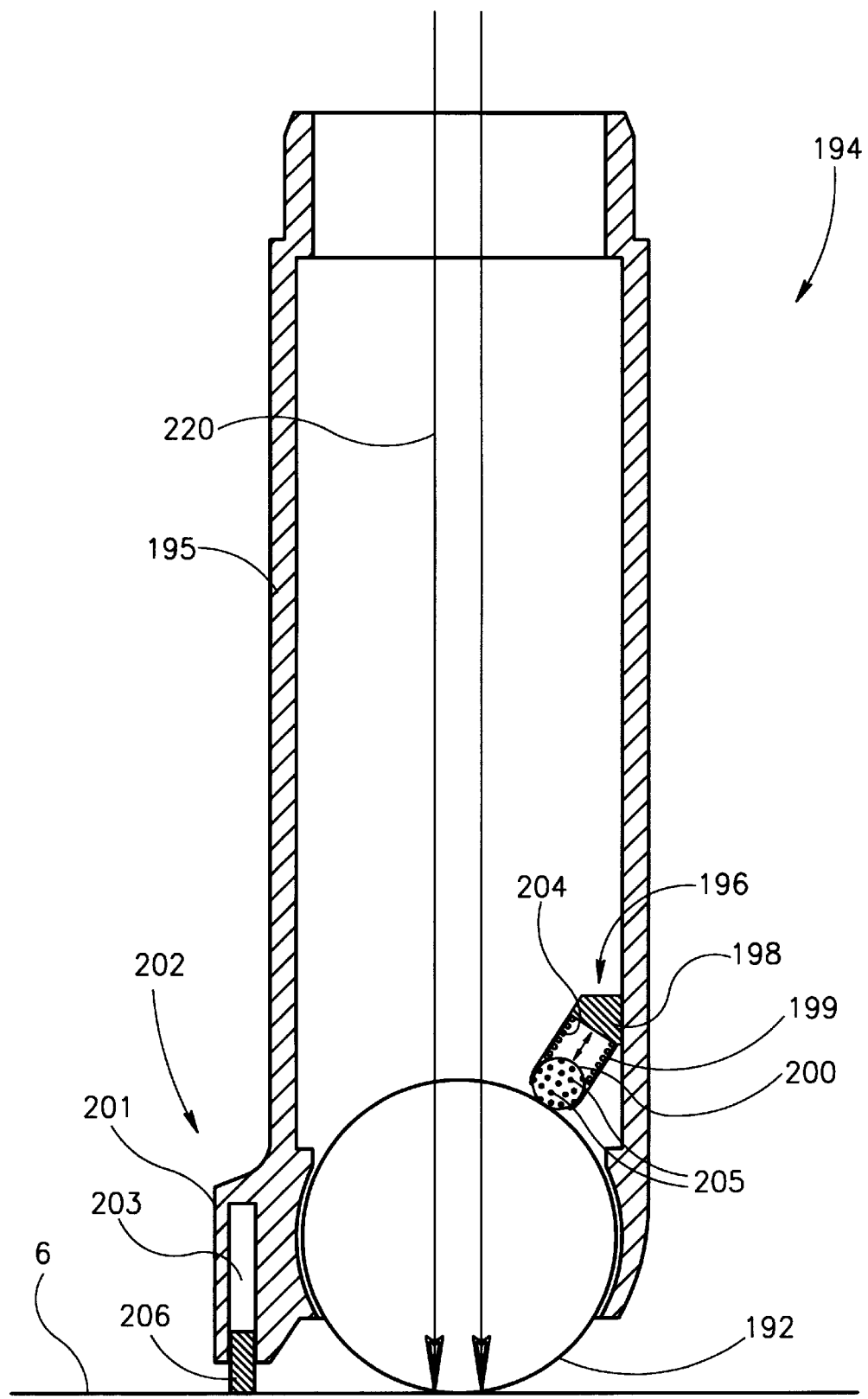
FIG. 15 is a schematic cross section illustrating a handpiece having a multi-directional sensor enabling controlling the exposure of a surface of a tissue to laser radiation while the handpiece is being moved in any orientation along the surface of the tissue and for marking the surface with a marker, in accordance with still another preferred embodiment of the present invention.

Reference is now made to FIGS. 14 and 15. FIG. 14 is a schematic cross section illustrating a handpiece 154 having a multi-directional sensor constructed and operative in accordance with another preferred embodiment of the present invention to control the exposure of a surface of a tissue to laser radiation while being moved in any orientation of the handle along the surface of the tissue. FIG. 15 is a schematic cross section illustrating a handpiece 194 having a multi-directional sensor for controlling the exposure of a surface of a tissue to laser radiation while being moved in any orientation of the handle along the surface of the tissue and for marking the surface with a marker, in accordance with still another preferred embodiment of the present invention.

The handpiece 154 includes a hollow member 155, and a sensor assembly 166 attached to one end of the hollow member 155. The sensor assembly 166 includes a housing 171 and a spherical rotatable member 172. The spherical rotatable member 172 is suitably attached within the housing 171 such that it can freely rotate in any selected direction. When the spherical rotatable member 172 is in contact with the surface 6, the handpiece 154 can be moved in any selected direction along the surface 6, causing the spherical rotatable member 172 to rotate within the housing 171. The sensor assembly 166 also includes an optical sensor 28 which operates as disclosed hereinabove for the handpiece 4 of FIG. 3.

The spherical rotatable member 172 is made of a suitable material such as metal or plastic. The spherical rotatable member 172 has a plurality of circular spots 175 painted or attached on its surface. The spots 175 have a light reflectivity which is substantially different than the reflectivity of the surface of the spherical member between the spots 175. The reflectivity of the spots 175 can be higher than the reflectivity of surface of the spherical member between the spots, mutatis mutandis. A feature of the sensor assembly 166 is that the spots 175 are isotropically distributed along the surface of the spherical rotatable member 172 in such a way that the average number of transitions between areas of different reflectivity values occurring per unit length when moving in any randomly selected direction along the surface of the rotatable spherical member 172 is constant irrespective of the direction of movement.

The sensor 28 illuminates the surface of the spherical rotatable member 172 with a light beam 168 and detects the changes in reflectivity occurring as the spots pass under the light beam 168 as disclosed hereinabove for the notches of the cogwheel shaped rotatable member 22 of sensor assembly 16 of FIG. 3. The sensor 28 thus sends "on" and "off" signals to the signal processor unit 14 (FIG. 1) through a suitable connecting cable (not shown) for calculating the distance traversed by the handpiece 154 on the surface 6, based on the known distribution of the spots 175 on the surface of the rotatable spherical member 172.

It is noted that, instead of the spots 175, the spherical rotatable member 172 can have notches or depressions within its surface (not shown) having a different reflectivity than the surface between the notches. Such notches will function similarly to the spots 175.

It is noted that the spots 175 or the notches disclosed hereinabove are preferably circular but can also have other suitable shapes as long as they are isotropically distributed along the surface and as long as their size is relatively small compared to the diameter of the spherical rotatable member 172.

The handpiece 154 can thus be moved along the surface 6 in any selected direction, while the longitudinal axis of the handpiece 154 along which axis the beams 180 are directed is substantially perpendicular to the surface 6, without the handpiece having to be oriented in a specific direction, while still maintaining a controlled exposure of the surface to light beams 180 as disclosed hereinabove.

It is noted that, while the sensor assembly 166 of the handpiece 154 is of FIG. 14 is implemented as a particular type of optical sensor, the sensor assembly 166 can be any suitable type of sensor such as an optical sensor or a suitable mechanical sensor that can sense the movement of the handpiece 154 along the surface 6, irrespective of the direction of movement selected.

Turning to FIG. 15, Handpiece 194 includes a hollow member 195 having a spherical rotatable member 192 suitably attached thereto such that spherical rotatable member 192 is freely rotatable in any selected direction. The spherical rotatable member 192 is made of a material which is transparent to the radiation which is irradiated from the radiation source which is connected to the handpiece such as a laser beam irradiated from a laser. For example, the spherical rotatable member 192 can be made from glass or transparent plastic depending on the particular wavelengths of the radiation radiated from the radiation source.

The handpiece 194 further includes a sensor assembly 196 suitably attached to the hollow member 195. The sensor assembly 196 includes a housing 199, a spherical rotatable member 200 and an optical sensor 198. The spherical rotatable member 200 has a plurality of spots or notches 205 formed on its surface, similarly to the spots or notches 175 of the spherical rotatable member 172 of FIG. 14. The spots or notches 205 are isotropically distributed along the surface of the spherical rotatable member 200. The spherical rotatable member can be made of a slightly resilient material such as rubber or plastic and is spring loaded by a spring 204 so that it is pressed against the surface of the spherical rotatable member 192.

When the spherical rotatable member 192 is placed in contact with the surface 6 and the handpiece 194 is moved along the surface 6, the spherical rotatable member 192 rotates causing the spherical rotatable member 200 to rotate. The sensing of the movement of the spherical rotatable member 200 by the is done similarly to the sensing of the movement of the spherical rotatable member 172 by optical sensor 198 as disclosed for sensor 28 of FIG. 15. The sensor 198 thus sends "on" and "off" signals to the signal processor unit 14 (FIG. 1) through a suitable connecting cable (not shown) for calculating the distance traveresed by the handpiece 154 on the surface 6 as disclosed hereinabove, taking into account the diameter of the spherical rotatable members 192 and 200 and the known distribution of the spots or notches 205 on the surface of the spherical rotatable member 200.

The handpiece 194 can thus be moved along the surface 6 in any selected direction, without the handpiece having to be oriented in a specific direction, while still maintaining a controlled exposure of the surface to light beams 220, as disclosed hereinabove.

The handpiece 194 also includes a marking device 202. Marking device 202 includes a replaceable container 201 containing a marker 203 therewithin. Marking device 202 further includes a marking tip 206 which is in contact with the surface 6 when the hand piece 194 is placed in contact therewith. When the handpiece 194 is moved along surface 6, the marking tip 206 transfers some of the marker 203 onto the surface 6, thus, depositing a visible marker film (not shown) thereupon. The visible marker film assists the operator in determining which areas of the surface 6 have already been exposed to radiation.

It is noted that, when light beams are passed from a light source such as a laser, through the hollow members 85, 105, 115 and 195 of the handpieces 84, 104, 114, and 194, respectively, the path of the beams may be distorted (not shown) when the beams pass through the transparent rotatable members 82, 102 and 192, which may also cause a change in the shape and size of the spot of light which is projected on the surface 6. (the distortion of the beams is not shown in any of the FIGS. 6, 9, 10, 11 and 15 for the sake of clarity of illustration). If necessary, these distortions can be substantially controlled and corrected by placing various optical elements within the hollow member 195 as disclosed hereinabove and illustrated in FIG. 4. A common feature of all the preferred embodiments of the handpiece of the present invention disclosed hereinabove is that, in all of them the handpiece can be used by first coating the surface of the tissue with a layer of a gel such as the ultrasound gel "Aquasonic clear" commercially available as product No. 0308 from Parker Laboratories, N.J., U.S.A., which is substantially transparent to the laser beam 20, and proceeding to operate the handpiece to irradiate the surface of the tissue as disclosed hereinabove for each of the different handpieces. The use of gel has the advantage of assisting in the cooling of the tissue which results in the same advantages as disclosed for handpiece 104 hereinabove.

It is noted that other suitable types of transparent gel can be used for cooling of the irradiated tissue.

It is further noted that, in accordance with a preferred embodiment of the present invention the laser used with the system is a pulsed laser.

It is still further noted that, in accordance with another preferred embodiment of the present invention the laser used with the handpiece is a continuous wave laser.

It will be appreciated to those skilled in the art that, while some of the preferred embodiments of the system and of the handpiece of the present invention are disclosed as using particular types of sensors, rotatable members, hollow rotatable members for cooling and marking devices, many other types of systems and handpieces can be constructed using various combinations of these components that are within the scope of the present invention.

It will also be appreciated by persons skilled in the art, that the present invention is not limited to what has been particularly shown and described hereinabove. Rather the scope of the present invention is defined by the claims which follow:

What is claimed is:

1. A system for providing a substantially homogenous exposure of a surface to light, the system comprising:
   a light delivery handpiece having two ends;
   a light source connected to a first end of said light delivery handpiece;
   a sensor assembly attached to a second end of said light delivery handpiece for sensing the distance moved by said second end along said surface; and
   a signal processing unit connected to said sensor assembly and said light source for decoding the output of said sensor assembly and for activating said light source when said second end moves a predetermined distance along said surface.

2. A system according to claim 1 wherein said predetermined distance is determined by the size and energy distribution profile of the spot of light produced by said light source on said surface.

3. A system according to claim 1 wherein said signal processing unit also provides a stop signal to an operator when said second end has moved a predetermined distance measured on said surface.

4. A system according to claim 1 wherein said signal processing unit activates said light source when said second end has moved said predetermined distance along said surface, only when manually activated by said operator, and wherein said stop signal is selected from the group consisting of an audible signal, a visible signal and a combination thereof.

5. A system according to claim 1 wherein said surface is the surface of tissue.

6. A system according to claim 1 wherein said light source is a pulsed laser.

7. A system according to claim 1 wherein said light source is a continuous wave laser.

8. A system according to claim 1 wherein said pulsed light source is an incoherent light source.

9. A system according to claim 1 further comprising a marking device for marking said surface with a visible marker indicating the part of said surface which has been exposed to light.

10. A system according to claim 1 further comprising a device for cooling said surface.

11. A system according to claim 1 and also comprising a beam delivery system connecting said first end of said light delivery handpiece to said light source.

12. A system according to claim 1 wherein said beam delivery system is selected from an articulated arm, an optical fiber, an optical fiber bundle and a hollow waveguide.

13. A handpiece comprising:
 a hollow member having a first end and a second end; and
 a sensor assembly attached to said first end of said hollow member for sensing the movement of said handpiece along a surface and for providing signals representing said sensed movement,
 wherein said sensor assembly is activated by a rotatable member, rotatable by moving said handpiece along said surface and
 wherein said second end of said hollow member is connectable to a light source.

14. A handpiece according to claim 13 wherein said hollow member also comprises at least one optical element for directing light from said light source to said surface.

15. A handpiece according to claim 14 wherein said at least one optical element is selected from an optical fiber, an optical fiber bundle, a hollow waveguide, a lens and any combination thereof.

16. A handpiece according to claim 13 wherein said rotatable member is rotatably attached to said first end of said hollow member, said rotatable member being made of a material which is substantially transparent to light emitted from said light source, said rotatable member being positioned at said first end such that the light emitted from said light source passes through said rotatable member prior to striking said surface.

17. A handpiece according to claim 16 wherein said transparent rotatable member is hollow, enabling a cooling fluid to be circulated therewithin for cooling said surface while said rotatable member is being in contact therewith.

18. A handpiece according to claim 13 and also comprising a marking device for marking said surface while said handpiece is being moved therealong.

19. A handpiece according to claim 13 wherein said second end of said hollow member is connectable to said light source through a scanner.

20. A handpiece according to claim 13 wherein said handpiece is stertilizable.

21. A handpiece according to claim 13 wherein said rotatable member is disposable.

22. A handpiece according to claim 13 wherein said rotatable member is sterilizable.

23. A handpiece according to claim 13 wherein said rotatable member is a spherical rotatable member, said spherical rotatable member being rotatable in any selected direction along said surface, whereby said handpiece is movable in said selected direction along said surface and said sensor provides signals representing said sensed movement in said selected direction.

24. A handpiece according to claim 23 wherein said handpiece can be oriented in any selected orientation relative to the direction of its movement along said surface while the longitudinal axis of said handpiece is being held substantially perpendicular to said surface.

25. A handpiece according to claim 13 wherein said surface is the surface of tissue.

26. A handpiece according to claim 13 wherein said light source is a pulsed laser.

27. A handpiece according to claim 13 wherein said light source is a continuous wave laser.

28. A handpiece according to claim 13 wherein said pulsed light source is an incoherent light source.

29. A handpiece according to claim 13 wherein said hollow member further comprises a visible mark for indicating the orientation required for moving said handpiece along said surface.

30. A handpiece according to claim 13 wherein the said hollow member is shaped to have a distinctly visible polarity for indicating the orientation required for moving said handpiece along said surface.

31. A handpiece comprising:
 a hollow member having a first end and a second end; and
 a sensor assembly attached to said first end of said hollow member for sensing the movement of said handpiece along a surface and for providing signals representing said movement;
 a marking device for marking said surface while said handpiece is being moved therealong, and
 wherein said second end of said hollow member is connectable to a light source.

32. A handpiece comprising:
 a hollow member having a first end and a second end; and
 a sensor assembly attached to said first end of said hollow member for sensing the movement of said handpiece along a surface and for providing signals representing said sensed movement,
 wherein said second end of said hollow member is connectable to a light source through a scanner.

33. A handpiece comprising;
 a hollow member having a first end and a second end; and
 a sensor assembly attached to said first end of said hollow member for sensing the movement of said handpiece along a surface and for providing signals representing said sensed movement,
 wherein said handpiece is sterilizable; and
 wherein said second end of said hollow member is connectable to a light source.

34. A handpiece comprising:
 a hollow member having a first end and a second end;
 a sensor assembly attached to said first end of said hollow member for sensing the movement of said handpiece along a surface and for providing signals representing said sensed movement; and a visible mark for indicating the orientation required for moving said handpiece along said surface, wherein said visible mark is attached to said sensor assembly; and wherein said second end of said hollow member is connectable to a light source.

35. A handpiece comprising:

a hollow member having a first end and a second end; and a sensor assembly attached to said first end of said hollow member for sensing the movement of said handpiece along a surface and for providing signals representing said sensed movement, wherein said hollow member is shaped to have a distinctly visible polarity for indicating the orientation required for moving said handpiece along said surface; and wherein said second end of said hollow member is connectable to a light source.

* * * * *